United States Patent
Wilson, Jr. et al.

[11] Patent Number: 5,962,364
[45] Date of Patent: Oct. 5, 1999

[54] PROCESS FOR SYNTHESIS OF MOLYBDENUM SULFIDE DIMERS

[75] Inventors: Robert B. Wilson, Jr., Palo Alto; Yuhua Du, Reseda; David Bomberger, Belmont, all of Calif.

[73] Assignee: BP Amoco Corporation, Chicago, Ill.

[21] Appl. No.: 08/903,054

[22] Filed: Jul. 30, 1997

[51] Int. Cl.[6] .............................. B01J 31/00; C07F 11/00
[52] U.S. Cl. ......................... 502/155; 502/159; 556/58
[58] Field of Search ................................. 502/155, 159; 556/58

[56] References Cited

U.S. PATENT DOCUMENTS

| | | | |
|---|---|---|---|
| 3,758,608 | 9/1973 | Rigdon et al. | 260/677 |
| 4,361,497 | 11/1982 | Boldt et al. | 502/159 |
| 4,547,321 | 10/1985 | Stiefel et al. | 556/14 |
| 4,681,958 | 7/1987 | Halbert et al. | 556/42 |
| 4,730,064 | 3/1988 | Halbert et al. | 556/15 |
| 5,391,791 | 2/1995 | Dubois et al. | 556/60 |
| 5,414,194 | 5/1995 | Dubois et al. | 585/855 |
| 5,430,225 | 7/1995 | Dubois et al. | 585/855 |

FOREIGN PATENT DOCUMENTS 62-277152  12/1987  Japan ..................... 502/155

OTHER PUBLICATIONS

L.–C. Song et al., Polyhedron, vol. 15, No. 17, pp. 2915–2921, 1996.

L.–C. Song et al., Polyhedron, vol. 16, No. 3, pp. 481–487, 1997.

L.–C. Song et al., Polyhedron, vol. 16, No. 13, pp. 2249–2255, 1997.

L.–C. Song et al., Inorg. Chim. Acta, vol. 256, pp. 129–135, 1997.

H. Brunner et al., J. Organomet. Chem., vol. 434, pp. 63–78, 1992.

M. Rakowski Dubois et al., J. Am. Chem. Soc., vol. 101, No. 18, pp. 5245–5251, Aug. 1979.

M. Rakowski Dubois et al., J. Am. Chem. Soc., vol. 102, No. 25, pp. 7456–7461, 1980.

P. Braterman et al., J. Chem. Soc., Dalton Trans., pp. 241–245, 1976.

J. Kotz et al., Organometallics, vol. 2, No. 1, pp. 68–79, Jan. 1983.

J. Birnbaum et al., Organometallics, vol. 10, No. 6, pp. 1779–1786, 1991.

B. Kaul et al., Organometallics, vol. 16, No. 8, pp. 1604–1611, 1997.

"Reactions of Cationic Dinuclear Molybdenum Complexes Containing $\mu$–Sulfido and $\mu$–Thiolate Ligands" by M. Rakowski DuBois, *Journal of Cluster Science*, vol. 7, No. 3, (1996), pp. 293–315.

"Kinetic Studies of Olefin Binding to Sulfido Sites in Dinuclear Molybdenum Complexes" by C.R. Koval, L.L.

(List continued on next page.)

*Primary Examiner*—Mark L. Bell
*Assistant Examiner*—J. Pasterczyk
*Attorney, Agent, or Firm*—Richard A. Kretchmer; James R. Henes; Frank J. Sroka

[57] ABSTRACT

A method for converting $[MoCp(CO)_3]_2$, in which at least one of the Cp groups has a substitutent having a carbonyl or carboxyl group and the compound has a Mo—Mo single bond, into a resinous supported material having repeating units of the formula $(MoCp)_2S_4$. The repeating units have four bridging sulfido ligands between the two molybdenum atoms, and the repeating units are joined to each other by bridging-sulfide ligands. The method comprises reacting the molybdenum carbonyl dimer with elemental sulfur in a solvent for the starting material at a temperature between 110–120° C. in the presence of a solid adsorbent support. The resinous material may be further hydrogenated, the hydrogenated material may be further reacted to form a material having a carboxyl-containing methanedithiolate ligand, and this latter material may be further hydrolyzed. The molybdenum sulfide dimers are useful for separation, purification, and recovery of unsaturated hydrocarbons.

19 Claims, 1 Drawing Sheet

OTHER PUBLICATIONS

Lopez, B.B. Kaul, S. Renshaw, K. Green, and M. Rakowski DuBois, *Organometallics* (*1995*), vol. 14, pp. 3440–3447.

"Synthesis of Water Soluble Sulfur–Bridged Molybdenum Dimers with Substituted Cyclopentadienyl Ligands" by J. Allshouse, Bharat B. Kaul, and M. Rakowski DuBois, *Organometallics* (*1994*), vol. 13, pp. 28–36.

"Role of [Cp*Mo($\mu$–S)]$_2$ S$_2$CH$_2$ in Dichloromethane Hydrogenolysis" by M. Maciejewski Farmer, R.C. Haltiwanger, F. Kvietok, and M. Rakowski DuBois *Organometallics* (*1991*), vol. 10, No. 12, pp. 4066–4069.

"Studies of the Protonation and Oxidation of Sulfido Ligands in Dinuclear Molybdenum Complexes" by J. Birnbaum, G. Goziela, M. Maciejewski, T. L. Tonker, R. C. Haltiwanger, and M. Rakowski DuBois, *Organometallics* (*1990*), vol. 9, pp. 394–401.

"Insertions of Unactivated Olefins into the Hydrosulfido Ligand of a Cationic Cyclopentadienylmolybdenum Complex" by J. Birnbaum, J. C. V. Laurie, and M. Rakowski Dubois, *Organometallics* (*1990*), vol. 9, pp. 156–164.

"Synthesis of Inequivalently Bridged Cyclopentadienyl Dimers of Molybdenum and a Comparison of Their Reactivities with Unsaturated Molecules and with Hydrogen" by Maryanne McKenna, Laura L. Wright, Douglas J. Miller, Linnea Tanner, R. C. Haltiwanger, and M. Rakowski DuBois, *J. Am. Chem. So.* (*1983*), vol. 105, pp. 5329–5337.

"Functionally Substituted Cyclopentadienyl Metal Compounds" by David W. Macomber, William P. Hart, and Marvin D. Rausch, *Advances in Organometallic Chemistry*, vol. 21, (1982), pp. 1–55.

"Syntheses, Structures, and Reactions of Molybdenum Complexes with Sulfido and Disulfido Ligands" by M. Rakowski DuBois, D. L. DuBois, M. C. VanDerveer, and R. C. Haltiwanger, *Inorganic Chemistry*, vol. 20, No. 9 (1981), pp. 3064–3071.

PROCESS FOR SYNTHESIS OF MOLYBDENUM SULFIDE DIMERS

FIELD OF THE INVENTION

The field of this invention relates to improved processes for preparation of molybdenum-sulfide dimer compounds. These dimer compounds are characterized by their ability to reversibly bind alkenes and/or their ability to react with alkynes. Molybdenum sulfide dimers prepared according to the present invention exhibit varying useful properties such as water solubility and ligand reactivity. More particularly, this invention concerns use of heterogeneous adsorbent in processes for chemical conversion in which a cyclopentadienyl molybdenum tricarbonyl dimer is converted to a supported resinous composition having repeating units in which the two cyclopentadienyl molybdenum units are connected by four sulfido bridging ligands. Repeating units of the resinous composition can have bridging sulfide ligands. Also included in this invention are such novel supported resinous compositions Molybdenum sulfide dimers synthesized according to this invention are particularly useful complex agents for purification of relatively impure olefins produced by thermal cracking of suitable hydrocarbon feedstocks.

BACKGROUND OF THE INVENTION

Olefin-paraffin separations represent a class of most important and also most costly separations in the chemical and petrochemical industry. Cryogenic distillation has been used for over 60 years for these separations. They remain to be the most energy-intensive distillations because of the close relative volatilities. For example, ethane-ethylene separation is carried out at about −25° C. and 320 psig in a column containing over 100 trays, and propane-propylene separation is performed by an equally energy-intensive distillation at about −30° C. and 30 psig.

Olefins are, generally, produced via catalytic cracking processes. Such processes produce refinery-grade olefins (65–70 purity). Currently. refinery grade olefins are further separated and purified using distillation columns to produce polymer-grade olefins (99.5% purity) or chemical-grade olefins (95% purity). Frequently two distillation columns must be employed. Each distillation step is expensive and energy intensive, and even incremental gains in purity greatly increase the costs of the olefin products.

Current theories for improving the economics of olefin separations and purifications suggest that a hybrid separation process be utilized. In addition to the conventional distillation step, some other chemically specific process would be utilized to enhance olefin purity for greatly reduced costs. Processes that have been suggested as potentially being amenable to the hybrid approach include: 1) a facilitated transport membrane using a chemically-specific complexing agent; 2) absorption/stripping with a chemical solvent; and 3) adsorption/desorption on a solid support.

Rationale for use of hybrid olefin separation processes is as follows: conventional separation technology can only achieve a certain level of separation per stage. This level of separation is not a constant for each stage. As higher purity levels are required, the number of stages increases rapidly. This also means a dramatic increase in the costs for additional processing equipment. On the other hand, a separation step using reversible chemical complexation obtains improved selectivity at the same time that the driving force of conventional olefin separation processes decreases. Although this is not intuitive, it occurs because there is a large excess of complexing agent present and the selective reaction becomes very efficient. The hybrid process, therefore, typically combines a conventional separation process to achieve a certain level of purity and follows it with a separation step using reversible chemical complexation to "polish" or further purify the desired product. See, Haggin, *Chem. & Eng. News.*, pg. 23–24 Feb. 25, 1991.

Previous reversible binding systems have used a complexation agent that contains a metal ion that has an affinity for the unsaturated hydrocarbon to be separated. Processes for separating unsaturated hydrocarbons from a gaseous hydrocarbon mixture by contacting the mixture with an aqueous solution of heavy metal salts capable of forming reversible complexes with the unsaturated hydrocarbons, whereby the unsaturated hydrocarbons are complexed and extracted by such aqueous solution, are known. Water-soluble silver or copper salts or complexes have been reported as being capable of forming reversible complexes with unsaturated hydrocarbons in such processes. Silver ion, $Ag(I)$, is known to be especially useful for the separation of olefins. However, at least some of such salts or complexes are reported to be adversely affected by certain materials that are frequently present in the gaseous mixtures from which the unsaturated hydrocarbons are to be separated or to form complexes with alkenes or alkynes that are thermally unstable.

$AgNO_3$ reacts, irreversibly, with sulfur compounds. Copper compounds are very susceptible to reactions with oxygen. water or sulfur compounds. Such reactions lead to very poor lifetimes in operation or, in the alternative, lead to the higher costs required for removing the compounds prior to separation and purification. Similar problems exist with acetylene (when purifying ethylene) and propyne (when purifying propylene). Again, the alkyne impurities increase costs either by greatly reducing the life of the complexing agent, or by the mechanism required to remove the alkyne prior to the separating process utilizing the complexing agent.

In a few instances, the ability of metal ions to bind reversibly to olefins has been utilized in olefin separation and purification systems. For example, olefin adducts of $Ag(I)$ ion have been used in chromatographic systems for the separation of olefins. More recently, aqueous silver nitrate solutions have been used to separate ethylene or propylene from purified multicomponent gas streams. See, U.S. Pat. No. 4,174,353 of Marcinkowsky et al. A major concern when using the silver/olefin adduct chemistry, is that the silver ion forms a complex with acetylene which is explosive when dry and rigorous methods must be employed to remove acetylene from any gas stream that will come in contact with the silver ion. A further problem associated with silver/olefin separation schemes is that the silver ion is rapidly poisoned by $H_2S$, a common impurity in gas associated with the thermal cracking of hydrocarbons.

Thus, it is highly desirable to develop improved complexing agents for use in the aforesaid processes for separating unsaturated hydrocarbons from hydrocarbon mixtures containing them. Potential which molybdenum-sulfide dimers have as complexation agents in part of a hybrid olefin separation process has been recognized. See, for example, U.S. Pat. Nos. 5,391,791 in the name of Mary Rakowski Dubois, Richard Noble and Carl Koval; 5,414,194; and 5,430,225 which describe molybdenum sulfide dimer compounds and their use in olefin separation and acetylene removal processes. The dimers act as complexation agents for the olefins and acetylenes wherein the sulfide ligands of the molybdenum-sulfide dimers are believed to act as the site of olefin binding. The binuclear sulfide bridged molybdenum dimers have the general formula where x is 0–3 and n is 0, +1, or −1. In addition, this structure can be modified in a limited number of ways, such as substitutions that can be made to the alkanedithiolate moiety R or to the cyclopentadienyl moiety $C_5H_5$, (or Cp) in order to enhance the water solubility of the dimer or to introduce chemically reactive ligands that can be used to incorporate the dimer within the matrix of polymeric materials, such as membranes. The patents define suitable water soluble molybdenum-sulfide dimers as including all compounds that contain molybdenum and sulfur and that are capable of forming chemically or thermally-reversible alkanedithiolate or alkenedithiolate complexes that have significant solubility in water or aqueous systems.

In contrast to the use of metal ion chemistry in olefin separation schemes, the molybdenum-sulfide dimers are unaffected by the presence of $H_2S$. In addition, the inventors of the present invention have also described how the ability of the molybdenum-sulfide dimers to bind and to subsequently reduce alkynes may be used in alkyne removal processes.

The dimeric complexation agents are disclosed as being useful in separation processes that include liquid/liquid, gas/liquid, liquid/solid and gas/solid separation procedures that are familiar to those skilled in the art. Separations by the use of the molybdenum-sulfide dimers that are disclosed include the separation of olefins from paraffins (for example, ethylene from ethane and propylene from propane), the separation of olefins (for example, ethylene from propylene), the separation of olefin isomers (for example, cis-2-butene from trans-2-butene), the separation of olefins from alkynes (for example, ethylene from acetylene and propylene from propyne), and the removal of alkynes from a gaseous hydrocarbon feed stream and the catalytic reduction of alkynes.

The molybdenum sulfide dimers disclosed in the aforesaid Dubois et al. patents were synthesized in accordance with the procedures of Dubois et al., J. Am. Chem. Soc., Volume 101, pages 5245–5252 (1979); Dubois et al., J. Am. Chem. Soc., Volume 102, page 7456 (1980); Dubois et al., Inorg. Chem., Volume 20, pages 3064–3071 (1981); M. McKenna et al., J. Am. Chem. Soc., Volume 105, pages 5329–5337 (1983); and J. Birnbaum et al., Organometallics, volume 10, pages 1779–1786 (1991). However, generally such syntheses are lengthy and complicated and afford a low yield of the desired product. Consequently, it is highly desirable to develop alternative processes for synthesis of molybdenum sulfide dimers that could be used as suitable complexation agents for the selective and reversible complexation of unsaturated hydrocarbons in the aforesaid processes for separating unsaturated hydrocarbons from multi-component gaseous mixtures containing them.

It is therefore a general object of the present invention to provide an improved process for synthesis of molybdenum sulfide dimers that affords a relatively uncomplicated synthesis while retaining their aforesaid desirable features.

More particularly, it is an object of the present invention to provide improved processes that substantially reduce the time required for preparation of the desired complexation agents which are soluble and stable in water and that selectively forms a reversible complex with an unsaturated hydrocarbon that is also soluble and stable in water.

It is another object of the present invention to provide improved processes that make more efficient use of reactants required to synthesis desired molybdenum sulfide dimers and thereby increase yields.

It is a further object of the present invention to provide an improved aforesaid process that employs a complexation agent whose stability and complexation activity are not adversely affected by other materials that are frequently present in the multi-component gaseous mixtures from which an unsaturated hydrocarbon is to be separated.

Other objects and advantages of the present invention will become apparent upon reading the following description and appended claims.

SUMMARY OF THE INVENTION

Objects of the invention are achieved by the process of the present invention for chemical conversion of a cyclopentadienyl molybdenum tricarbonyl first dimer in which at least one cyclopentadienyl moiety contains at least one carboxyl- or carbonyl- containing ring substituent and in which the two cyclopentadienyl molybdenum units of the dimer are directly connected through the two molybdenum atoms, to a resinous composition having repeating units in which the two cyclopentadienyl molybdenum units are connected by four sulfido bridging ligands and the repeating units have bridging sulfide ligands. The process comprises reacting the first dimer with elemental sulfur at a temperature in the range of from about 110° C. to about 120° C. in an effective solvent for the first dimer and in the presence of a solid adsorbent for the resinous composition, such that the resinous composition is deposited thereon to form a supported resinous composition.

Figure 1A:
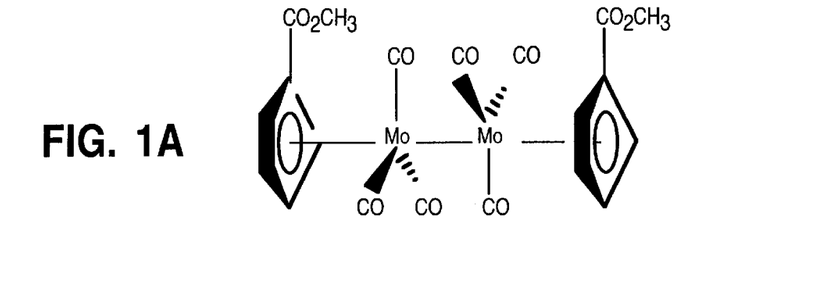
Figure 1B:
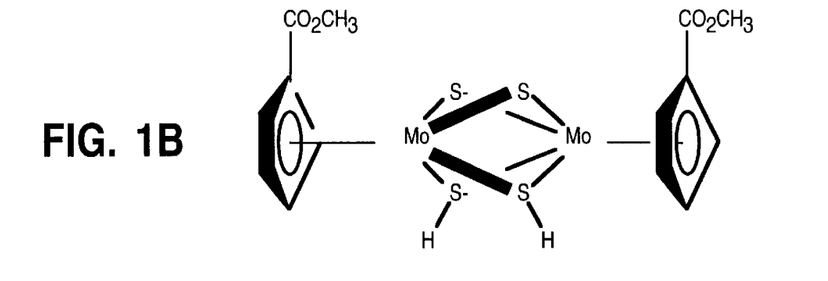
Figure 2A:
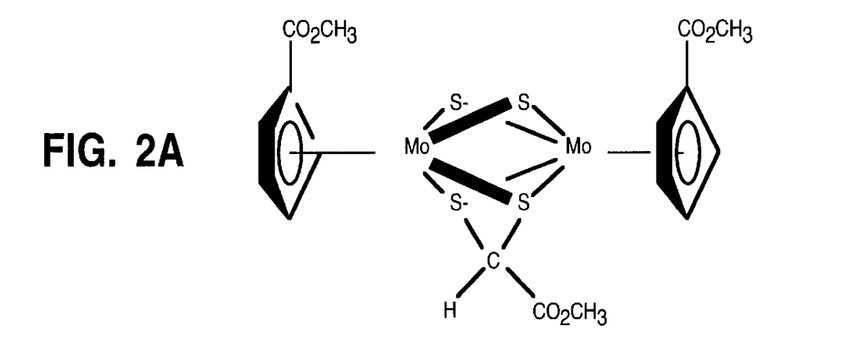
Figure 2B:
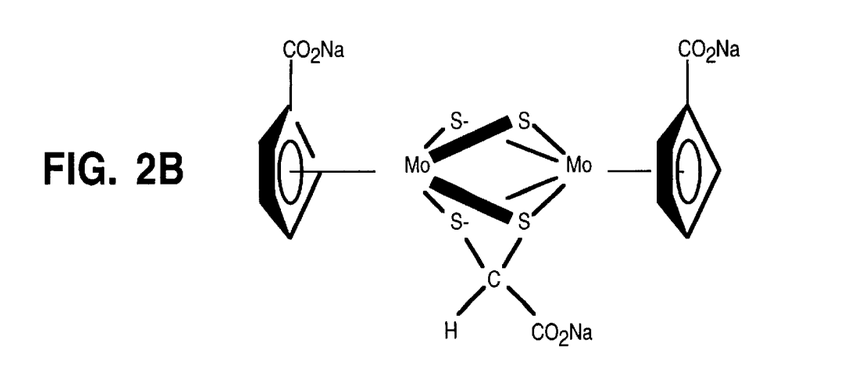

This invention is an improvement over the original Sulfurization process to synthesize $[MeO_2C\text{-}CpMo\mu\text{-}S)(\mu\text{-}SH)]_2$ or FIG. 1 (B). In the original process, as described in Allshouse, J.; Bharat B. Kaul; M. Rakowski DuBois, "Synthesis of Water Soluble Sulfur-Bridged Molybdenum Dimers with Substituted Cyclopentadinyl Ligands" *Organometallics* 13, pp 28–36 (1994) (Allshouse et al.), the polymer product, $[(MeO_2C\text{-}CpMo)_2(\mu\text{-}S)_4]_nS_x$, formed as a rubbery solid that is not only chunky but also sticks to the flask wall. The product needs to be scraped off the flask and ground to fine powders for the hydrogenation reaction. Such practice poses a big obstacle in scaling up the synthesis. In this invention, we introduced excess silica gel (90–200 mesh) to the reaction solution. We found that the polymer product deposited to the surface of silica gel rather than to the flask wall. The final product is evenly dispersed to the silica gel as fine particles.

In another aspect processes according to the present invention further comprise hydrogenating the supported resinous composition whereby the bridging sulfide ligands are removed as $H_2S$ and two sulfido ligands are converted to hydrosulfido ligands resulting in formation of a second dimer where the two cyclopentadienyl molybdenum units are connected by two sulfido bridging ligands and two hydrosulfido bridging ligands.

In another aspect processes according to the present invention further comprise reacting the second dimer with a carboxyl-containing material capable of undergoing reaction with the hydrosulfido bridging ligands, whereby the hydrosulfido bridging ligands in the second dimer are converted to a carboxyl-containing methanedithiolate bridging ligand to form a resulting third dimer.

In yet another aspect processes according to the present invention further comprise hydrolysis of the third dimer whereby each ester group on the cyclopentadienyl moiety and in the methanedithiolate bridging ligand in the dimer produced is acid- or base- hydrolyzed to its corresponding carboxylic acid or carboxylate salt to form a fourth dimer.

In still another aspect the invention is a process for chemical conversion of a cyclopentadienyl molybdenum sulfur dimer in which at least one cyclopentadienyl moiety contains at least one carboxyl- or carbonyl- containing ring substituent and in which the two cyclopentadienyl molybdenum units of the dimer are connected through two sulfido bridging ligands and two hydrosulfido bridging ligands, the process comprising reacting the cyclopentadienyl molybdenum sulfur dimer in an effective solvent for the dimer and at temperatures in a range of from about 15° C. to about 30° C. with a carboxyl-containing material capable of undergoing reaction with the hydrosulfido bridging ligands, whereby the hydrosulfido bridging ligands in the dimer are converted to a carboxyl-containing methanedithiolate bridging ligand to form a resulting dimer. This process further comprises, preferably, hydrolysis of the resulting dimer whereby each ester group on the cyclopentadienyl moiety and in the methanedithiolate bridging ligand in the resulting dimer is acid- or base- hydrolyzed to its corresponding carboxylic acid or carboxylate salt to form a fourth dimer.

Another aspect of special significance is a process for hydrolysis of a cyclopentadienyl molybdenum sulfur dimer in which at least one cyclopentadienyl moiety contains at least one carboxyl- or carbonyl- containing ring substituent and in which the two cyclopentadienyl molybdenum units of the dimer are connected through two sulfido bridging ligands and a carboxyl-containing methanedithiolate bridging ligand, whereby each ester group on the cyclopentadienyl moiety and in the methanedithiolate bridging ligand is acid- or base- hydrolyzed to its corresponding carboxylic acid or carboxylate salt, the process comprising initiating the hydrolysis in a predominantly methanol solvent and completing the hydrolysis in a predominantly aqueous solution.

The instant invention includes a composition comprising a supported resinous composition having repeating units in which two cyclopentadienyl molybdenum units are connected by four sulfido bridging ligands and the repeating units have bridging sulfide ligands, the composition formed by reacting a cyclopentadienyl molybdenum tricarbonyl first dimer in which at least one cyclopentadienyl moiety contains at least one carboxyl- or carbonyl- containing ring substituent and in which the two cyclopentadienyl molybdenum units of the dimer are directly connected through the two molybdenum atoms, with elemental sulfur at a temperature in the range of from about 110° C. to about 120° C. in an effective solvent for the first dimer and in the presence of a solid adsorbent for the resinous composition, such that the resinous composition is deposited thereon to produce the supported resinous composition.

For a more complete understanding of the present invention, reference should now be made to the embodiments illustrated in greater detail in the accompanying drawing and described below by way of examples of the invention.

BRIEF DESCRIPTION OF THE FIGURE

The appended claims set forth those novel features which characterize the present invention. The present invention itself, as well as advantages thereof, may best be understood, however, by reference to the following brief description of preferred embodiments taken in conjunction with the annexed drawings depicting selected dimer structures, in which:

FIG. 1 (A) is an illustration depicting a structure for a first dimer [$MeO_2CCpMo(CO)_3$]$_2$ and (B) is a structure for a second dimer [$MeO_2CCpMo(\mu$-$S)(\mu$-$SH)$]$_2$, and FIG. 2 (A) is an illustration depicting a structure for a third dimer [$MeO_2C$-$CpMo(S)$]$_2(S_2O_2Me)_2$ and (B) is a structure for the dimer [$NaO_2CCpMo(S)$]$_2(S_2CHCO_2Na)$.

BRIEF DESCRIPTION OF THE INVENTION

Support materials are, advantageously, selected from the group consisting of alumina, silica, carbon, clay and zeolites (molecular sieves). Surface areas of support materials are, preferably, in a range of from about 10 to about 1,000 square meters per gram as measured by the BET gas adsorption method.

A preferred class of adsorbents useful in processes according the invention, comprises at least about 90 weight percent of a gamma alumina having surface area in a range of from about 80 to about 500 square meters per gram as measured by the BET gas adsorption method, and contains less than 500 parts per million by weight of a sulfur-containing component, calculated as elemental sulfur. More preferred are the adsorbent which comprises at least about 90 weight percent of a gamma alumina having surface area in a range of from about 150 to about 350 square meters per gram as measured by the BET gas adsorption method, and wherein the metal dispersed on the support material is palladium, and the absorbent has a palladium content in a range of from about 0.01 to about 10 percent based on the total weight of the adsorbent.

It has been found that the process of this invention possesses a number of significant advantages over other art recognized processes in which the sulfurization is conducted without a solid adsorbent for the resulting resinous composition which is believed to comprise a sulfide bridged polymer. First, the use of the solid matrix, i.e., the high surface area adsorbent as exemplified by silica gel, alumina, silica-alumina, diatomaceous earth, activated clays, such as Porocel clay, a hard, highly adsorbent activated bauxite marketed by the Englehard Minerals and Chemicals or, montmorillonite clay, fuller's earth, etc. to support the sulfide bridged polymer, permits the sulfide bridged polymer to be handled as if it were a high surface particulate solid. Second, the carrier acts to limit the free sulfide bridged polymer in the liquid phase of the mixture with a resultant advantage in product work-up. Third, the dispersed condition of the supported sulfide bridged polymer provides more intimate contacting between the polymer and reactants during hydrogenation than would be available with bulk sulfide bridged polymer.

The preparation of the free-flowing, granular adsorbent supported resinous composition utilized in this invention can be conveniently accomplished, for example, by mixing together a cyclopentadienyl molybdenum tricarbonyl first dimer with elemental sulfur at a temperature in the range of from about 110° C. to about 120° C. in an effective solvent for the first dimer and a granular, high surface area adsorbent having a mesh size of from about 4 to about 300 and, preferably, from about 8 to about 16, with sulfuric acid. The high surface area adsorbent employed must be substantially free of physically adsorbed water. The mixing time required is related to the mesh size of the particular adsorbent employed. The quantity of granular adsorbent used can be varied widely and generally the amount employed is such that the adsorbent supported resinous composition will contain from about 5 to about 75 weight percent of sulfide bridged polymer and preferably from about 15 to about 50 weight percent sulfide bridged polymer on the same basis.

No after-treatment of the adsorbent supported resinous composition is required and after the free-flowing granular product has been formed, the composition which is readily handled is ready for immediate use. Alternatively, the adsorbent supported resinous composition can be stored for a considerable period of time provided contact with moisture is not permitted.

A preferred class of carbons useful herein are materials disclosed in commonly assigned U.S. Pat. No. 4,082,694 to Arnold N. Wennerberg and Thomas M. O'Grady, which patent is incorporated herein by reference. Such suitable active carbon products are produced from carbonaceous material by a staged temperature process which provides improved yield and processability during manufacture. A source of carbonaceous material, such as crushed coal, coal coke, petroleum coke or a mixture thereof, is heated with agitation in the presence of a substantial weight ratio of hydrous potassium hydroxide at a first lower temperature to dehydrate the combination thereafter the temperature is raised to a second higher temperature to activate the combination which is thereafter cooled and washed to remove inorganic matter and form a high surface area active carbon having a cage-like structure exhibiting micro-porosity, good bulk density and Total Organic Carbon Index.

Generally, the term "molecular sieve" includes a wide variety of positive-ion-containing crystalline materials of both natural and synthetic varieties. They are generally characterized as crystalline aluminosilicates, although other crystalline materials are included in the broad definition. The crystalline aluminosilicates are made up of networks of tetrahedra of $SiO_4$ and $AlO_4$ moieties in which the silicon and aluminum atoms are cross-linked by the sharing of oxygen atoms. The electrovalence of the aluminum atom is balanced by the use of positive ions, for example, alkali-metal or alkaline-earth-metal cations.

Zeolitic materials, both natural and synthetic, useful herein have been demonstrated in the past to have catalytic capabilities for many hydrocarbon processes. Zeolitic materials, often referred to as molecular sieves, are ordered porous crystalline aluminosilicates having a definite structure with large and small cavities interconnected by channels. The cavities and channels throughout the crystalline material are generally uniform it, size allowing selective separation of hydrocarbons. Consequently, these materials in many instances have come to be classified in the art as molecular sieves and are utilized, in addition to the selective adsorptive processes, for certain catalytic properties. The catalytic properties of these materials are also affected, to some extent, by the size of the molecules which are allowed selectively to penetrate the crystal structure, presumably to be contacted with active catalytic sites within the ordered structure of these materials.

In the past various molecular sieve compositions natural and synthetic have been found to be useful for a number of hydrocarbon conversion reactions. Among these are alkylation, aromatization, dehydrogenation and isomerization. Among the sieves which have been used are Type A, X, Y and those of the MFI crystal structure, as shown in "Atlas of Zeolite Structure Types," Second Revised Edition 1987, published on behalf of the Structure Commission of the International Zeolite Associates and incorporated by reference herein. Representative of the last group are ZSM-5 and AMS borosilicate molecular sieves.

Prior art developments have resulted in the formation of many synthetic crystalline materials. Crystalline aluminosilicates are the most prevalent and, as described in the patent literature and in the published journals, are designated by letters or other convenient symbols. Exemplary of these materials are Zeolite A (Milton, in U.S. Pat. No. 2,882,243), Zeolite X (Milton, in U.S. Pat. No.2,882,244), Zeolite Y (Breck, in U.S. Pat. No. 3,130,007), Zeolite ZSM-5 (Argauer, et al., in U.S. Pat. No. 3,702,886), Zeolite ZSM-II (Chu, in U.S. Pat. No. 3,709,979), Zeolite ZSM-12 (Rosinski, et al., in U.S. Pat. No. 3.832,449), and others.

Manufacture of the ZSM materials utilizes a mixed base system in which sodium aluminate and a silicon containing material are mixed together with sodium hydroxide and an organic base, such as tetrapropylammonium hydroxide and tetrapropylammonium bromide, under specified reaction conditions, to form the crystalline aluminosilicate, preferably a crystalline metallosilicate exhibiting the MFI crystal structure.

A preferred class of molecular sieves useful, according to the present invention, are crystalline borosilicate molecular sieves disclosed in commonly assigned U.S. Pat. No. 4,268,420, U.S. Pat. No. 4,269,813, U.S. Pat. No. 4,292,457, and U.S. Pat. No. 4,292,458 to Marvin R Klotz, which are incorporated herein by reference.

Surface area of adsorbents can be determined by the Brunaur-Emmett-Teller (BET) method or estimated by a simpler Point B method. Adsorption data for nitrogen at the liquid nitrogen temperature, 77° K., are usually used in both methods. The Brunaur-Emmett-Teller equation, which is well known in the art, is used to calculate the amount of nitrogen for mono-layer coverage. The surface area is taken as the area for mono-layer coverage based on the nitrogen molecular area, 16.2 square Angstroms, obtained by assuming liquid density and hexagonal close packing. In the Point B method, the initial point of the straight portion of the Type II isotherm is taken as the completion point for the mono-layer. The corresponding amount adsorbed multiplied by molecular area yields the surface area.

A high-surface-area $\gamma$-$Al_2O_3$ is a preferred adsorbent for purification of olefins in accordance with this invention.

Synthesis of molybdenum sulfide dimers according to the invention comprises steps which are, generally, carried out in a liquid phase comprising a suitable solvent having a normal boiling point temperature of less than about 175° C. Suitable organic solvents comprise from 2 to about 9 carbon atoms, and for several critical reactions are, preferably, ring compounds.

Solvents suitable for sulfurization according to the invention comprise, preferably, one or more compound selected from the group consisting of toluene, ethylbenzene, isopropylbenzene, n-propylbenzene, tetrahydrofuran, methylene chloride, p-xylene, m-xylene, and o-xylene. More preferably, the sulfurization reaction is conducted in solvent comprising toluene and under reflux conditions..

Solvents suitable for hydrogenation according to the invention comprise, preferably, one or more compound selected from the group consisting of toluene, methylene chloride, tetrahydrofuran, and dimethyl ether. Hydrogenation in an effective solvent for the second dimer is, preferably, carried out at a pressure in the range of from about ambient (about 0 psig) to about 100 pounds per square inch gauge and a temperature in the range of from about 50° C. to about 85° C.

Suitable carboxyl-containing materials capable of undergoing reaction with the hydrosulfido bridging ligands of the second dimer, whereby the hydrosulfido bridging ligands in the second dimer are converted to a carboxyl-containing methanedithiolate bridging ligand to form a resulting third dimer, include, preferably, carboxyl-containing material comprises a compound represented by formula $X_2CH$ $CO_2CH_3$ or $R$ $(CO_2CH_3)_2$ where R is selected from the group consisting of and X is a halogen selected from the group consisting of Cl and Br. More preferably, the carboxyl-containing material comprises $Cl_2CHCO_2CH_3$.

Reactions converting the second dimer to the third dimer are, preferably, carried out in an effective solvent for the second dimer and at a temperature in the range of from about 15° C. to about 30° C. Solvents suitable for this aspect of the invention comprise, preferably, at least one member of the group consisting of tetrahydrofuran, dimethyl ether, and diethyl ether.

In the hydrolysis according to the invention, whereby each ester group on the cyclopentadienyl moiety and in the methanedithiolate bridging ligand in the dimer is acid- or base- hydrolyzed to its corresponding carboxylic acid or carboxylate salt, the critical elements are initiation of the hydrolysis in a predominantly methanol solvent and its completion in predominantly aqueous solution. Hydrolysis in accordance with the invention is, preferably, carried out at temperatures in a range of from about 60° C. to about 90° C.

The hydrolyzed dimer is, advantageously, purified by reprecipitation from a methanol-diethyl ether solvent.

EXAMPLES OF THE INVENTION

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

General

Synthesis of $[MeO_2CCpMo(CO_3)]_2$

Sodium hydride (2.5 g, 0.1 mol) was added to a solution of freshly cracked cyclopentadiene (10 mL, 0.12 mol) in distilled THF(300 mL) inside a glove-box. This solution was stirred under nitrogen with an oil bubbler overnight. Degassed dimethyl carbonate (27 mL, 0.3 mol) was then added. This solution was refluxed for 24 h. After this time period, the pink solution was allowed to cool to room temperature and molybdenum hexacarbonyl (30 g, 0.11 mol) was added against a flow of nitrogen to the solution. This mixture was refluxed for three days. After this time period, a degassed solution of iron (III) sulfate pentahydrate (40 g) in water (500 mL) and acetic acid (30 mL) were added to the yellow-orange tetrahydrofuran solution via cannula over a period on one hour. The resultant slurry was allowed to stir until gas evolution had ceased, and then the flask was placed in an ice bath and allowed to sit for 30 min. The red crystalline solid $[MeO_2CCpMo(CO_3)]_2$ was filtered from the solution. The solid was washed with two portions of water (10 mL), two portions of methanol (10 mL), two portions of pentane (20 mL). Yield, 36 g, purity, 80% according to $^1H$ NMR. Percent yield based on $Mo(CO)_6$ 80%.

Note: It has also been demonstrated that this reaction could be carried out by using a technical grade molybdenum hexacarbonyl, $Mo(CO)_6$ containing about 5% $Cr(CO)_6$, with similar yield. This technical grade $Mo(CO)_6$ costs considerably less than the 98% and greater $Mo(CO)_6$ used in the original procedure.

The invention cuts down the processing cost for scaling up the synthesis of $[NaO_2CCpMo(S)]_2(S_2CHCO_2Na)$.

EXAMPLE 1

Preparation of $[(MeO_2CCpMo)_2(\mu-S)_4]_nS_x/SiO_2$.

This example illustrates preparation of supported resinous intermediate having repeating units in which the two cyclopentadienyl molybdenum units are connected by four sulfido bridging ligands and the repeating units have bridging sulfide ligands by the process of reacting a first dimer, $[MeO_2CCpMo(CO)_3]_2$, with elemental sulfur at a temperature in the range of from about 110° C. to about 120° C. in an effective solvent for the first dimer and in the presence of a solid adsorbent, silica.

Sulfurization: Toluene (600 mL) was introduced to a solid mixture of sulfur (5.12 g, 20.0 mmol) and [$MeO_2CCpMo(CO)_3$]$_2$ (12.0 g, 20.0 mmol) in a 1000-mL flask. To this suspension was added 20 g silica (90–200 mesh) which had been heated in an oven at 100° C. for 1 hour. The resulting slurry was refluxed under nitrogen for 3 days. The light brown solution was then filtered through a medium porosity fritted funnel, and the black fine particles were washed with several portions of dichloromethane. After drying in vacuo, the coated silica gel weighed 29.5 g. IR (Nujol mull): 800(m), 960(m), 1070(s, br), 1200(s, sh, br), 1620(w), 1700(m)

EXAMPLE 2

Preparation of $[MeO_2CCpMo(\mu-S)(\mu-SH)]_2/SiO_2$

This example illustrates direct hydrogenation, i.e. without preparative reaction with a light olefin, of the supported resinous intermediate whereby the bridging sulfide ligands are removed as $H_2S$ and two sulfido ligands are converted to hydrosulfido ligands resulting in formation of a second dimer where the two cyclopentadienyl molybdenum units are connected by two sulfido bridging ligands and two hydrosulfido bridging ligands.

Hydrogenation: The dried black solid supported on silica (6.3 g) was combined with 400 mL of dichloromethane, and the slurry was heated (50° C.)under hydrogen pressure (2.7–6.8 atm) in a Parr hydrogenation apparatus. The apparatus was shaken continuously by a rocker-type shaker. After 3 days, the apparatus was vented in a hood. An aqueous $CuSO_4$ solution was used to trap the $H_2S$ released. The red purple solution was filtered through a medium porosity fritted funnel. The solvent was removed from the filtrate by vacuum to yield a purple powder. Yield, 1.9 g, 72% based on [$MeO_2CCpMo(CO)_3$]$_2$.

Hydrogenations were, also, performed in a thick wall glass container under lower hydrogen pressures (1.5 and 3.0 atm) with similar yields (70% to 86%).

EXAMPLE 3

Preparation of $[(MeO_2C-CpMo)_2(\mu-S)_4]_nS_x$

Sulfurization: Toluene (600 mL) was introduced to a solid mixture of sulfur (5.1 g, 20.0 mol) and [$MeO_2CCpMo(CO)_3$]$_2$ (12.1 g, 20.0 mmol) in a 1000 mL flask. The resulting slurry was refluxed under nitrogen for 3 days. The black solution was then filtered through a medium porosity fritted funnel, and the black-purple resinous solid was washed with 200 mL dichloromethane until the washes became colorless. Yield, 11.5 g.

EXAMPLE 4

Preparation of [MeO$_2$CCpMo($\mu$-S)($\mu$-SH)]$_2$

Hydrogenation: The dried black-purple resinous solid (4.0 g), [(MeO$_2$CCpMo)$_2$($\mu$-S)$_4$]$_n$S$_x$, was first ground to fine powder and then combined with 400 mL of dichloromethane. The slurry was heated (50° C.) under hydrogen pressure (2.7–6.8 atm) in a Parr hydrogenation apparatus. The apparatus was shaken continuously by a rock-type shaker. After 3 days, the apparatus was vented in a hood. An aqueous CuSO$_4$ solution can be used to trap the H$_2$S released. The red purple solution was filtered through a medium porosity fritted funnel. The solvent was removed from the filtrate by vacuum to yield a purple powder. Yield, 3.2 g.

EXAMPLE 5

Preparation of [MeO$_2$CCpMo(S)]$_2$(S$_2$CHCO$_2$Me)

The dimer prepared as in Example 4, [MeO$_2$CCpMo($\mu$-S)($\mu$-SH)]$_2$ (0.83 g, 1.46×10–3 mol) was dissolved in 100 mL distilled tetrahydrofuran after stirring over a period of 45 min. To this purple solution was added Cl$_2$CHCO$_2$CH$_3$, 0.15 mL, 1.46×10–3 mol), followed by addition of freshly prepared 1.2M solution of NaOMe (6 mL) in methanol drop-wise over a period of 20 min. The solution turned from purple to green in 10 min. The deep-green solution was stirred at room temperature for 3 h, and then filtered through a medium porosity fritted funnel. The solvent was removed in vacuo. The resulting green solid residue was vacuum dried. The $^1$H NMR of this green solid indicated that it is [MeO$_2$CCpMo(S)]$_2$(S$_2$CHCO$_2$Me), ca. 80% purity. The green product is stable under nitrogen both in the solid state and in CHCl$_3$ solution for at least 3 weeks. This green product was found to be thermallly stable up to 70° C. for at least 24 h.

EXAMPLE 6

Preparation of [NaO$_2$CCpMo(S)]$_2$(S$_2$CHCO$_2$Na)

Green solids from Example 5, [MeO$_2$CCpMo(S)]$_2$(S$_2$CHCO$_2$Me) were suspended in 140 mL of methanol. A solution of NaOH (0.42 g) in 10 mL of water was added. The mixture was refluxed for 1 day, resulting in a blue-green solution. Then the methanol solvent was pumped off. To the resulting deep blue residue was added 100 mL water under nitrogen atmosphere. The intermediate became quite water soluble at this stage and all of the residue dissolved. The deep blue solution was then heated to 110° C. and stirred for 1.5 days. At this stage NaHCO$_3$ (1.4 g) was added to the solution, and the mixture was further stirred for 2 hours. The blue-green solution was filtered through a fritted funnel. Solvent was evaporated from the blue solution to give a blue solid. The blue solid was dissolved in 100 mL of methanol and filtered to remove an insoluble brown solid. To the dark blue filtrate was added 100 mL diethyl ether. A fine blue precipitate formed and was collected by filtration. The blue product was dried in vacuo for 24 h. Yield: 0.56 g. Percent yield based on the amount of [MeO$_2$CCpMo($\mu$-S)($\mu$-SH)]$_2$: 60%.

These examples illustrate critical aspects of processes to prepare [NaO$_2$CCpMo(S)]$_2$(S$_2$CHCO$_2$Na) in accordance with the invention. Significant improvement on both yield and synthesis time has been achieved. The overall yield increased from about 10 percent to about 30 percent, and the synthesis time decreased from 22 days to 15 days as compared to Allshouse et al., *Organometallics* 13, pp 28–36 (1994).

According to the original synthesis, the conversion of [MeO$_2$CCpMo($\mu$-S)($\mu$-SH)]$_2$ to [MeO$_2$C-CpMo(S)]$_2$ (S$_2$CHCO$_2$Me) was the least efficient step in the entire synthesis with a yield of only 35%. During the reaction, [MeO$_2$C-CpMo(S)]$_2$ (S$_2$CHCO$_2$Me) was produced as an intermediate, which was, however, regarded as unstable. Reaction of ethylene with this intermediate was, therefore, used to form a stable ethylene adduct, (MeO$_2$CCpMo)2 (SC$_2$H$_4$S)(S$_2$CHCO$_2$Me). The ethylene adduct then underwent hydrolysis to form the final product, [NaO$_2$CCpMo (S)]$_2$(S$_2$CHCO$_2$Na). The yield from [MeO$_2$CCpMo($\mu$-S)$\mu$-SH)]$_2$ to the final product was 23%.

We have isolated and characterized the complex [MeO$_2$CCpMo(S)]$_2$(S$_2$CHCO$_2$Me) and found it to be stable both in solution and in the solid state. According to out invention the [MeO$_2$CCpMo(S)]$_2$(S$_2$Me) complex was directly hydrolyzed to yield the final product, [NaO$_2$CCpMo (S)]$_2$(S$_2$CHCO$_2$Na). Formation of the ethylene adduct is not required. The yield from [MeO$_2$C-CpMo($\mu$-S)($\mu$-SH)]$_2$ to the final product was improved to 60% as compared to the original 23%..

Also, according to the original synthesis, the hydrolysis of (MeO$_2$CCpMo)$_2$(SC$_2$H$_4$S)(S$_2$CHCO$_2$Me) in KOH solution was used to obtain product. Methanol with a small amount of water was used as the solvent. The hydrolysis required 7 days under reflux conditions, followed by neutralization with NaHCO$_3$ for 2 more days.

In the improved processes of the invention, water is used as the solvent for the hydrolysis of [MeO$_2$CCpMo(S)]$_2$ (S$_2$CHCO$_2$Me) after partial hydrolysis in methanol. Hydrolysis efficiency improved dramatically in water under reflux conditions. Hydrolysis time was shortened to 2.5 days as compared to the original 9 days.

Examples have been presented and hypotheses advanced herein in order to better communicate certain facets of the invention. The scope of the invention is determined solely by the scope of the appended claims.

For the purposes of the present invention, "predominantly" is defined as more than about fifty percent. "Substantially" is defined as occurring with sufficient frequency or being present in such proportions as to measurably affect macroscopic properties of an associated compound or system. Where the frequency or proportion for such impact is not clear substantially is to be regarded as about twenty percent or more. The term "Essentially" is defined as absolutely except that small variations which have no more than a negligible effect on macroscopic qualities and final outcome are permitted, typically up to about one percent.

That which is claimed is:

1. A process for chemical conversion of a cyclopentadienyl molybdenum tricarbonyl first dimer having the formula [MoCp(CO)$_3$)]$_2$ wherein Cp represents a cyclopentadienyl moiety, in which first dimer at least one cyclopentadienyl moiety contains at least one carboxyl- or carbonyl- containing ring substituent and in which the two cyclopentadienyl molybdenum tricarbonyl units of the first dimer are directly connected by a single bond between the two molybdenum atoms, to a resinous composition having repeating units having the formula (MoCp)$_2$S$_4$ and in each of which repeating units the two cyclopentadienyl molybdenum units are connected through four sulfido bridging ligands and the repeating units are connected by bridging sulfide ligands, the process comprising reacting the first dimer with elemental sulfur at a temperature in the range of from about 110° C. to about 120° C. in an effective solvent for the first dimer and in the presence of a solid adsorbent support for the resinous composition produced, such that the resinous composition produced is deposited thereon to form a supported resinous composition.

2. The process of claim 1 wherein the solvent comprises toluene, p-xylene, m-xylene, o-xylene, ethylbenzene, isopropylbenzene, n-propylbenzene, tetrahydrofuran or methylene chloride.

3. The process of claim 1 wherein the reaction is conducted in solvent comprising toluene and under reflux conditions.

4. The process of claim 1 wherein the solid adsorbent support is particulate.

5. The process of claim 4 wherein the solid adsorbent support comprises aluminum oxides, carbon, clays, silica or zeolites.

6. The process of claim 4 wherein the solid adsorbent support comprises silica or alumina.

7. The process of claim 4 wherein the solid adsorbent support comprises at least about 90 weight percent of an alumina having surface area in a range of from about 1 to about 500 square meters per gram as measured by the BET gas adsorption method.

8. The process of claim 1 wherein the solid adsorbent support is employed in amounts such that the weight ratio of the first dimer to the adsorbent is in the range of from about 0.6 to about 0.3.

9. The process of claim 1 further comprising hydrogenating the supported resinous composition produced whereby the bridging sulfide ligands connecting the repeating units are removed as H$_2$S and two sulfido bridging ligands connecting the aforesaid two cyclopentadienyl molybdenum units are converted to hydrosulfido ligands resulting in formation of a second dimer in which the aforesaid two cyclopentadienyl molybdenum units are connected by two sulfido bridging ligands and two hydrosulfido bridging ligands.

10. The process of claim 9 wherein the supported resinous composition is hydrogenated in an effective solvent for the second dimer at a pressure in the range of from about 15 to about 100 pounds per square inch gauge and a temperature in the range of from about 50° C. to about 85° C.

11. The process of claim 10 wherein the hydrogenation is performed in a solvent comprising toluene, methylene chloride, tetrahydrofuran or dimethyl ether.

12. The process of claim 9 further comprising reacting the aforesaid second dimer with a carboxyl-containing material capable of undergoing reaction with the hydrosulfido bridging ligands in the second dimer to thereby convert the hydrosulfido bridging ligands in the second dimer to a carboxyl-containing methanedithiolate bridging ligand in a resulting third dimer, wherein the aforesaid carboxyl-containing material comprises a compound represented by formula X$_2$CHCO$_2$CH$_3$ or R(CO$_2$CH$_3$)$_2$ where R is selected from the group consisting of and X is a halogen selected from the group consisting of Cl and Br.

13. The process of claim 9 further comprising reacting the aforesaid second dimer with a member of the group consisting of CH$_2$CHSO$_3$Na and CH$_2$CHPO$_3$Na$_2$ containing materials which are capable of undergoing reaction with the hydrosulfido bridging ligands, whereby the hydrosulfido bridging ligands in the second dimer are converted to a corresponding sulfate- or phosphate- containing bridging ligand to form a resulting fifth dimer, in an effective solvent for the second dimer and at temperatures in a range of from about 15° C. to about 30° C.

14. The process of claim 12 wherein the carboxyl-containing material comprises Cl$_2$CHCO$_2$CH$_3$.

15. The process of claim 14 wherein the reaction converting the second dimer to the third dimer is carried out in an effective solvent for the second dimer and at a temperature in the range of from about 15° C. to about 30° C.

16. The process of claim 15 wherein the solvent employed in the conversion of the second dimer to the third dimer comprises tetrahydrofuran, dimethyl ether or diethyl ether.

17. The process of claim 12 further comprising hydrolysis of the aforesaid third dimer whereby any ester group on the cyclopentadienyl moiety and in the methanedithiolate bridging ligand in the third dimer is acid- or base-hydrolyzed to its corresponding carboxylic acid or carboxylate salt to form a fourth dimer.

18. The process of claim 17 wherein the hydrolysis is initiated in a predominantly methanol solvent and completed in predominantly aqueous solution and the hydrolysis is carried out at temperatures in a range of from about 60° C. to about 90° C.

19. The process of claim 18 wherein the fourth dimer is purified by reprecipitation from a methanol-diethyl ether solvent.

* * * * *

UNITED STATES PATENT AND TRADEMARK OFFICE
CERTIFICATE OF CORRECTION

PATENT NO.: 5,962,364

DATED: Oct. 5, 1999

INVENTOR(S): Robert B. Wilson, Jr., Yuhua Du, David Bomberger

Page 1 of 3

It is certified that error appears in the above-identified patent and that said Letters Patent is hereby corrected as shown below:

| Col. | Line | |
|---|---|---|
| IN THE ABSTRACT: | | "bridging-sulfide ligands." <br> should read: <br> "bridging sulfide ligands." |
| 4 | 32 | "[MeO$_2$C-C$_p$Mo$\mu$-S)"... <br> should read: <br> "[MeO$_2$C-C$_p$Mo($\mu$-S)"... |

UNITED STATES PATENT AND TRADEMARK OFFICE
CERTIFICATE OF CORRECTION

PATENT NO.: 5,962,364
DATED: Oct. 5, 1999
INVENTOR(S): Robert B. Wilson, Jr., Yuhua Du, David Bomberger It is certified that error appears in the above-identified patent and that said Letters Patent is hereby corrected as shown below:

| Col. | Line | |
|------|------|---|
| 8 | 19 | "Marvin R Klotz,"<br><br>should read:<br>"Marvin R. Klotz," |
| 9 | 64 | " $^1$H NMR."<br><br>should read:<br>--(1)H NMR--. |
| 11 | 39 | "in $CHCl_3$ solution"<br><br>should read:<br>"in $CDCl_3$ solution" |

UNITED STATES PATENT AND TRADEMARK OFFICE
CERTIFICATE OF CORRECTION

PATENT NO.: 5,962,364

DATED: Oct. 5, 1999

INVENTOR(S): Robert B. Wilson, Jr., Yuhua Du, David Bomberger

It is certified that error appears in the above-identified patent and that said Letters Patent is hereby corrected as shown below:

| Col. | Line | |
|---|---|---|
| 12 | 22 | "($S_2$Me) complex" should read: "($S_2$CHCO$_2$Me) complex" |
| 13 | 23 | "comprises material selected from the group consisting of silica or alumina." should read: "comprises silica or alumina." |

Signed and Sealed this

Fifth Day of September, 2000

Attest:

Q. TODD DICKINSON

Attesting Officer

Director of Patents and Trademarks